United States Patent [19]

Korte et al.

[11] Patent Number: 5,679,848
[45] Date of Patent: Oct. 21, 1997

[54] PROCESS FOR THE PREPARATION OF TEREPHTHALIC ACID AND ITS ISOMERS

[75] Inventors: Hermann-Josef Korte, Haltern; Anton Schoengen, Witten-Bommern; Christoph Schwarz, Marl; Thomas Jostmann, Dülmen, all of Germany

[73] Assignee: Huels Aktiengesellschaft, Marl, Germany

[21] Appl. No.: 588,311

[22] Filed: Jan. 18, 1996

[30] Foreign Application Priority Data

Jan. 24, 1995 [DE] Germany .......... 195 02 122.3
Oct. 2, 1995 [DE] Germany .......... 195 36 814.2

[51] Int. Cl.$^6$ .................................. C07C 51/09
[52] U.S. Cl. ................................... 562/483
[58] Field of Search ........................ 562/483

[56] References Cited

U.S. PATENT DOCUMENTS 4,302,595  11/1981  Schoengen et al. ............ 562/483
4,578,510   3/1986  Doerr .

FOREIGN PATENT DOCUMENTS 0 464046   1/1992  European Pat. Off. .
1 618 503   1/1971  Germany .
29 16 197  10/1980  Germany .
29 38 163   4/1981  Germany .
29 42 859   4/1981  Germany .
30 11 858  10/1981  Germany .
30 41 293   6/1982  Germany .
30 44 617   6/1982  Germany .
34 07 912   5/1985  Germany .
40 26 733   2/1992  Germany .

*Primary Examiner*—Samuel Barts
*Attorney, Agent, or Firm*—Oblon, Spivak, McClelland, Maier & Neustadt, P.C.

[57] ABSTRACT

A process for the preparation of terephthalic acid (TA) from pure dimethyl terephthalate (DMT) and/or DMT intermediate product by hydrolysis in a countercurrent reactor at a conversion of greater than 99% and crystallization to give the solid product, characterized in that the sum of the stripping steam (S) and reaction water (W) satisfies the relationship $$L \leq S+W \leq 2L,$$

wherein (L) represents the amount of water necessary to keep the terephthalic acid (TA) produced largely in solution during the reaction and in the bottom of the reactor, and the terephthalic acid produced is crystallized in a crystallization which is free from washing stages.

20 Claims, 2 Drawing Sheets

1

PROCESS FOR THE PREPARATION OF TEREPHTHALIC ACID AND ITS ISOMERS

BACKGROUND OF THE INVENTION

Field of the Invention

The invention relates to a process for the preparation of terephthalic acid (TA) from dimethyl terephthalate (DMT) and/or a DMT intermediate product by hydrolysis in a countercurrent reactor with complete or almost complete conversion and crystallization to give solid product.

DISCUSSION OF THE BACKGROUND

Terephthalic acid (TA) and dimethyl terephthalate (DMT) are prepared on a large industrial scale in numerous plants world-wide. DMT and TA which is of high purity (PTA) and extremely high purity (PTA-p) are important starting compounds for the preparation of polyesters. The fields of use of polyesters for fibers and films, inter alia for photographic films and magnetic tapes or bottles of polyethylene terephthalate, to name only a few, have been known for a long time.

The current Witten DMT process for the preparation of DMT or DMT intermediate product comprises (see EP-PS 0 464 046, DE-OS 40 26 733 both incorporated herein by reference) essentially the process steps of oxidation of para-xylene (p-X) and para-toluic acid methyl ester (p-TE) with subsequent purification of the waste gas esterification of the reaction products from the oxidation with methanol separation of the so-called crude ester into
 a) a fraction which is recycled into the oxidation,
 b) a crude DMT fraction with more than 99% by weight of DMT and
 c) a high-boiling residue fraction, including working up thereof, purification of the crude DMT fraction, for example by washing, recrystallization and purification by distillation.

Terephthalic acid can be prepared from DMT or from DMT-rich fractions by controlled hydrolysis in a manner known per se (see "Terephthalsäure und Isophthalsäure (Terephthalic acid and isophthalic acid)", Ullman Vol. 22, 4th Edition, pages 519–528; DE-OS 29 16 197; DE-OS 29 38 163; DE-OS 29 42 859; DE-OS 30 11 858; DE-OS 30 41 293; DE-OS 30 44 617; DE-OS 34 07 912 all incorporated herein by reference).

Pure DMT and/or DMT intermediate product and/or isomers thereof (isophthalic acid, orthophthalic acid) are thus reacted in these processes by a hydrolysis which is as complete as possible, inter alia by the hydrolysis intermediate product monomethyl terephthalate (MMT) and/or its isomers, to give TA and/or isomers thereof. Methanol and dimethyl ether are formed as by-products.

It is also known that this reaction can be carried out batchwise in a stirred tank reactor or continuously in a cascade of stirred tanks, it being possible for the reaction equilibrium to be shifted in the direction of the product by removal of methanol, for example by stripping or distillation, or of TA from the liquid phase, for example by conversion to the solid. Operating the hydrolysis reaction in a countercurrent reactor with continuous removal of methanol is known in the art.

In the conventional processes, high amounts of impurities in the hydrolysis intermediate product at the reactor discharge are accepted, since virtually complete conversion can be achieved only with a very high energy input, for example in the form of stripping steam. In order to achieve the desirable or commercially available final purity in the solid TA product, expensive crystallization with washing must be provided in all the customary processes.

DE-PS 30 44 617, incorporated herein by reference, discloses a process for the preparation of TA by hydrolysis of DMT at a conversion of greater than 90% in a countercurrent reactor. The countercurrent reactor is followed by a multi-stage crystallization which includes several washing stages. This process can be operated only with high energy input, since in addition to the energy input for generation of stripping steam, considerable amounts of hot washing water are required here for the washing stages in the crystallization, which is operated under pressure. Furthermore, the expenditure on apparatus for the crystallization with the associated washing stages and the subsequent working up of the waste water is very high here.

OBJECTS OF THE INVENTION

One object of the invention is to provide a process which allows TA to be prepared in commercially usual purities (i.e., MTA, PTA and PTA-P) in a simple and economic manner.

BRIEF DESCRIPTION OF THE DRAWINGS

The invention will now be further described by reference to the appended drawings, wherein.

DETAILED DESCRIPTION OF THE INVENTION

Figure 1:
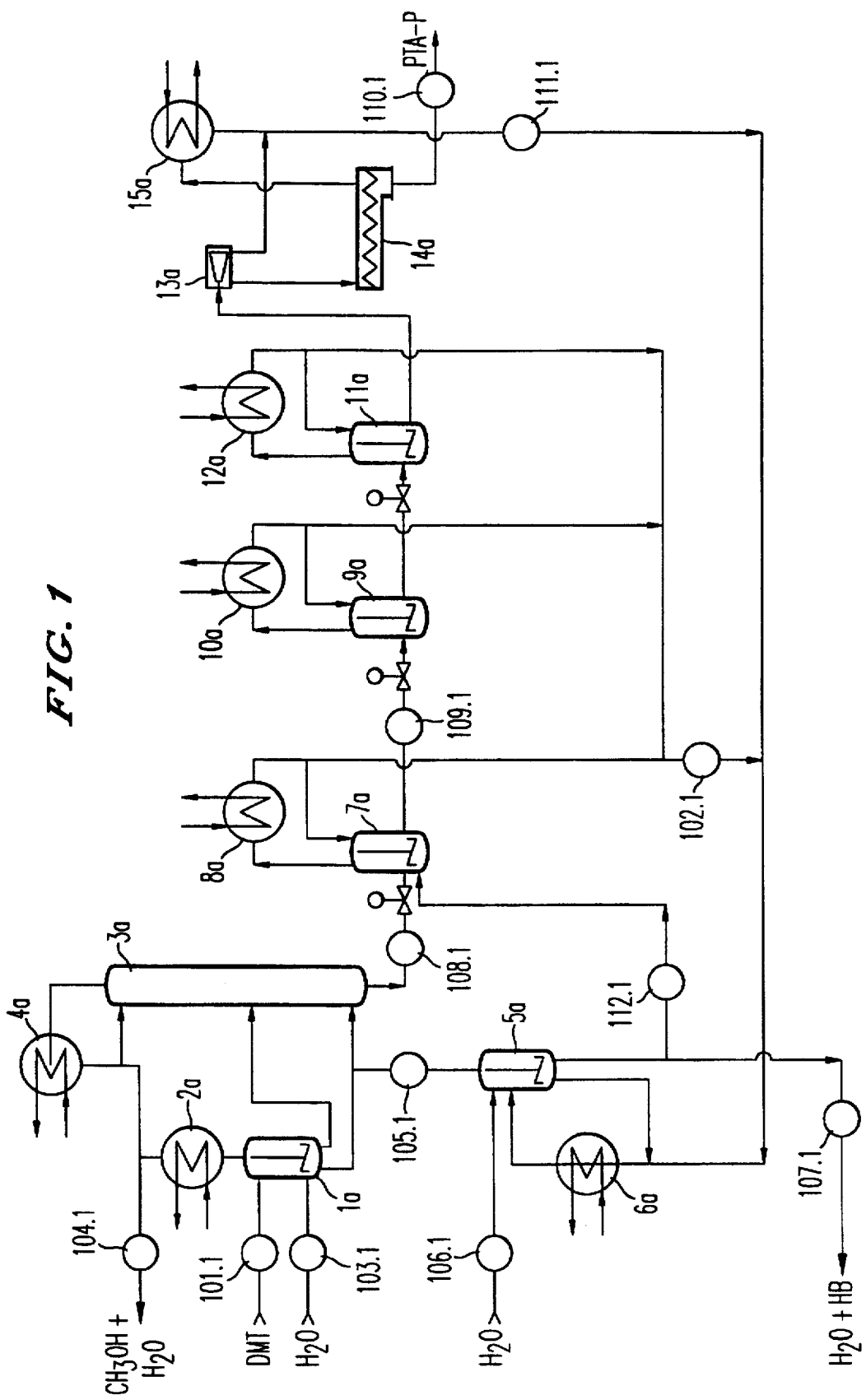
FIG. 1 shows a flow diagram of a preferred embodiment of the process according no the invention, where 1a: Preliminary reactor
2a: Condenser
3a: Countercurrent reactor
4a: Condenser, coupled
5a: Evaporator
6a: Heat exchanger
7a, 9a, 11a: Crystallization tank, stirrable
8a, 10a, 12a: Condensers
13a: Decanter
14a: Drier
15a: Condenser

It has now been found that it is possible to prepare TA in up to a very high purity and in an outstanding yield with a significantly lower energy input than in comparable DMT hydrolysis processes, inter alia for the generation of stripping steam, and without particular expenditure in crystallization, i.e. the expenditure for the provision of hot washing water and the need to work up spent quantities of washing water can be eliminated in the present process. It has thus been found, surprisingly, that the suitable combination of co-ordinated process steps, including hydrolysis in a countercurrent reactor, with the generation of stripping steam and the working up of methanol coupled to the hydrolysis reactor in some particular embodiments, and crystallization without the washing of the TA produced in the crystallization—leads to this particularly advantageous result. Another advantage which can be realized by the present process is virtually closed water circulation, which, inter alia, has a very positive effect on the environmental friendliness of the process.

The present invention therefore relates to a process for the preparation of terephthalic acid (TA) from pure dimethyl terephthalate (DMT) and/or DMT intermediate products by hydrolysis of these starting materials in a countercurrent reactor to a conversion of greater than 99% with crystallization to give solid product, which is characterized in that the sum of the stripping steam (S) and reaction water (W) satisfies the relationship $$L \leq S+W \leq 2L,$$

wherein (L) represents the amount of water necessary to keep the terephthalic acid (TA) produced largely in solution during the reaction and in the bottom of the reactor, where S, W and L are by weight, and the terephthalic acid produced is crystallized in a crystallization which is free from washing stages. Reaction water (W) in the present process is to be understood as meaning the water content which is fed externally to the countercurrent reactor in liquid form, for example via the stripping steam generator and/or a preliminary reactor.

DMT hydrolysis in a countercurrent reactor is in general carried out by introducing DMT and/or DMT-containing fractions from the top of the reactor and down to the middle region of the reactor and introducing stripping steam from the lower part of the reactor, preferably at the base of the hydrolysis reactor.

A countercurrent reactor useful for the present process suitably has 20 to 200 plates, and the countercurrent reactor is preferably equipped with more than 40 and up to 200 exchange plates.

In the process according to the invention, a preliminary reactor is preferably used in the form of a stirred tank or a cascade of stirred tanks or a flow tube, it being entirely possible for the amount employed and the mixing ratio of the educts as well as the operation of the plant to be widely variable. In this case, methanol is suitably removed from the circulation in or after the preliminary reactor and can be recycled into the DMT process.

The countercurrent reactor is in general operated in a temperature range of between 350° and 180° C. under a pressure which is necessary to maintain a liquid phase in the bottom of the reactor. In the process according to the invention, the reactor is suitably charged with a reflux which is capable of keeping the TA in the bottom of the reactor in solution. For example, the solubility of TA in water (L) is: 1.6% by weight at a temperature of 200° C. and under a pressure of 17 bar; 20% by weight at a temperature of 265° C. and under a pressure of 55 bar; 50% by weight at a temperature of 290° C. and under a pressure of 80 bar.

The methanol obtained in the process according to the invention is preferably worked up in the methanol working up step in the top part of the reactor and can be employed again in the DMT plant.

The reaction water from the process according to the invention is preferably employed again for mixing with DMT and/or directly in the reactor, the ratio of reaction water (W) to stripping steam (S), i.e., (W):(S) based on the weight, preferably being in the range from 1:1 to 4:1, particularly preferably 1:1 to 1.5:1, especially preferably 1:1.

The weight ratio of stripping steam (S) employed to DMT in the process according to the invention (i.e., (S):(DMT)) is preferably 1:1 to 6:1, particularly preferably 2:1 to 4:1.

Preferably, vapors which essentially comprise a methanol/water vapor mixture, are removed from the reactor via the top and condensed.

In the process according to the invention, high-quality steam which is suitable for further use, for example for use in the DMT plant or, preferably, as stripping steam using a heat pump, is preferably generated during partial or total condensation of the vapors leaving the reactor, it being possible for all or some of the liquid phase generated to be recycled to the reactor.

TA is obtained as the reaction product in the bottom of the reactor, efforts in general being made for the product to be present largely in dissolved form. Nevertheless, solids can partly be obtained during the hydrolysis.

In order to be able to achieve a high to very high product purity, a DMT conversion of significantly more than 99% is necessary in the process according to the invention. It may be advantageous for DMT which is as pure as possible already to be employed in the preliminary reactor in the process according to the invention.

In the process according to the invention, the content of monomethyl terephthalate (MMT) in the aqueous solution in the bottom of the reactor is preferably depleted to 5000 to 10 ppm by weight, particularly preferably to less than 900 to 10 ppm by weight, especially preferably to less than 50 ppm by weight, by stripping by means of steam.

The TA-containing aqueous solution in the bottom of the reactor is in general converted at a temperature of 350° to 180° C., under a pressure which is necessary to maintain a liquid phase, in a one- or multi-stage crystallization which is free from washing stages.

The crystallization of the TA is in general carried out at a temperature in the range from 300° to 100° C. In the one- or multi-stage crystallization of the process according to the invention, water is preferably removed from the circulation as a condensate at various temperature levels and is recycled to the process.

The water obtained in the crystallization can be separated off in any suitable manner, recycled to the process and employed in any desired ratios for the generation of the stripping steam and/or reaction water.

Preferably, in the process according to the invention, traces of impurities ("high boilers" = HB, cf. FIG. 1 and 2) are removed from circulation via the generation of stripping steam. In this procedure, preferably some or all of the bottom product is removed from the circulation and the remainder is recycled to the process.

The TA obtained in the crystallization of the process according to the invention, i.e. PTA (high purity terephthalic acid) or PTA-P (very high or extremely high purity terephthalic acid), is as a rule removed from the process by customary separation processes (for example filters, such as felt and drum filters, pressure filters, pressure centrifuges or one- or multi-stage decanters, such as pressure decanters, in particular sieve decanters) and drying processes (for example tube driers, current driers, fluidized bed driers) and many others.

Isophthalic acid (IRA) and orthophthalic acid (OTA) or mixtures thereof, or mixtures thereof with TA, can likewise be obtained from the particular methyl esters or mixtures thereof, inter alia from dimethyl isophthalate (DMI) and from dimethyl orthoterephthalate (DMO), by controlled hydrolysis as in the process according to the invention.

The process according to the invention has several particular advantages over the known processes, including:

- simple process structures which, by the omission of process stages such as, for example, countercurrent washing in the crystallization and a multi-stage cascade of reactors or separate distillation of the hydrolysis methanol, to comparatively low investment costs. An above-mentioned mixing reactor as a preliminary reactor can also be dispensed with, if necessary;
- commercially usual to very high purities of TA, also in respect of MMT, in spite of the lower energy consumption compared with comparison processes;
- easy handling of the product in the reaction sector, for example by a procedure in a completely dissolved range, but also by the possible omission of pressure-increasing pumps in the reaction sector;
- closed water circulation with minimal use of demineralized fresh water, and therefore no polluted waste water and lower energy consumption;
- high flexibility in respect of the purity of TA as a function of the energy consumption;
- high degree of adaptation to location conditions by possible adaptation of the desired energy consumption via investment expenditure.

EXAMPLES

The present invention is illustrated in more detail by the following non-limiting examples:

Example 1:

This example describes a preferred mode of operation of the process according to the invention in which the added water and DMT are added via the preliminary reactor, the evaporation rate in the generation of stripping steam is about 90%, no high-boiling constituents are removed from the circulation from the bottom product of the generation of stripping steam.

Example 1 is best explained a by reference to a plant according to the flow diagram in FIG. 1, in which DMT (substance stream 101.1) and added water (substance stream 103.1) are fed to the reactor 3a via the preliminary reactor 1a. The vapors are condensed in the condenser 4a, an adequate portion is removed as distillate (substance stream 104.1) and the remaining portion of the condensed liquid is introduced to the reactor as a reflux. The vapors produced in the preliminary reactor are condensed in the condenser 2a and separated off together with the other distillate (substance stream 104.1). All the methanol of the reaction is contained in the substance stream 104.1 and is passed into the methanol distillation of the DMT plant. From there, the water contained in the substance stream 104.1 is recycled back to the hydrolysis process with the substance stream 103.1. The substance stream 103.1 also comprises the water added on during the hydrolysis and any amounts of water contained in the product streams removed from the circulation. In this example, the substance stream 107.1 is employed at 0 kg/hour. No other water (substance stream 106.1) is fed in. The stripping steam (substance stream 105.1) is generated in the evaporator 5a with the heat exchanger 6a. It is remarkable that MMT is converted virtually completely into TA under the conditions which apply for generation of the stripping steam. The bottom product of the evaporator 5a is passed with substance stream 112.1 into the crystallizer 7a, in which the reaction product (substance stream 108.1) produced in the reactor 3a is also let down. The vapors formed are condensed in the condenser 8a and recycled back to the tank 7a. The stirred tanks 9a and 11a with the condensers 10a and 12a are further cooling or crystallization stages. It is remarkable that an MMT content in % or ppm by weight which is one quarter of the value in the liquid phase is established under the crystallization conditions prevailing here as long as the value at the discharge of the reactor is less than 1000 ppm. The crystal suspension formed in the crystallization is separated in the decanter 13a. The solid phase is freed in the drier 14a from still adhering residual moisture and removed from the circulation as solid TA, the quality obtained corresponding to highly pure PTA-P. The vapors from the drying are condensed in the condenser 15a and pumped together with the filtrate of the centrifuge 13a as substance stream 111.1 into the stripping steam generator 5a. In the present example, the water circulation over the process is closed.

The temperatures and the amounts stated for the substance streams—including the components contained therein from Example 1 are summarized in Table 1, the amounts stated in each case relating to a substance stream of 1000 kg of TA per hour.

Figure 2:
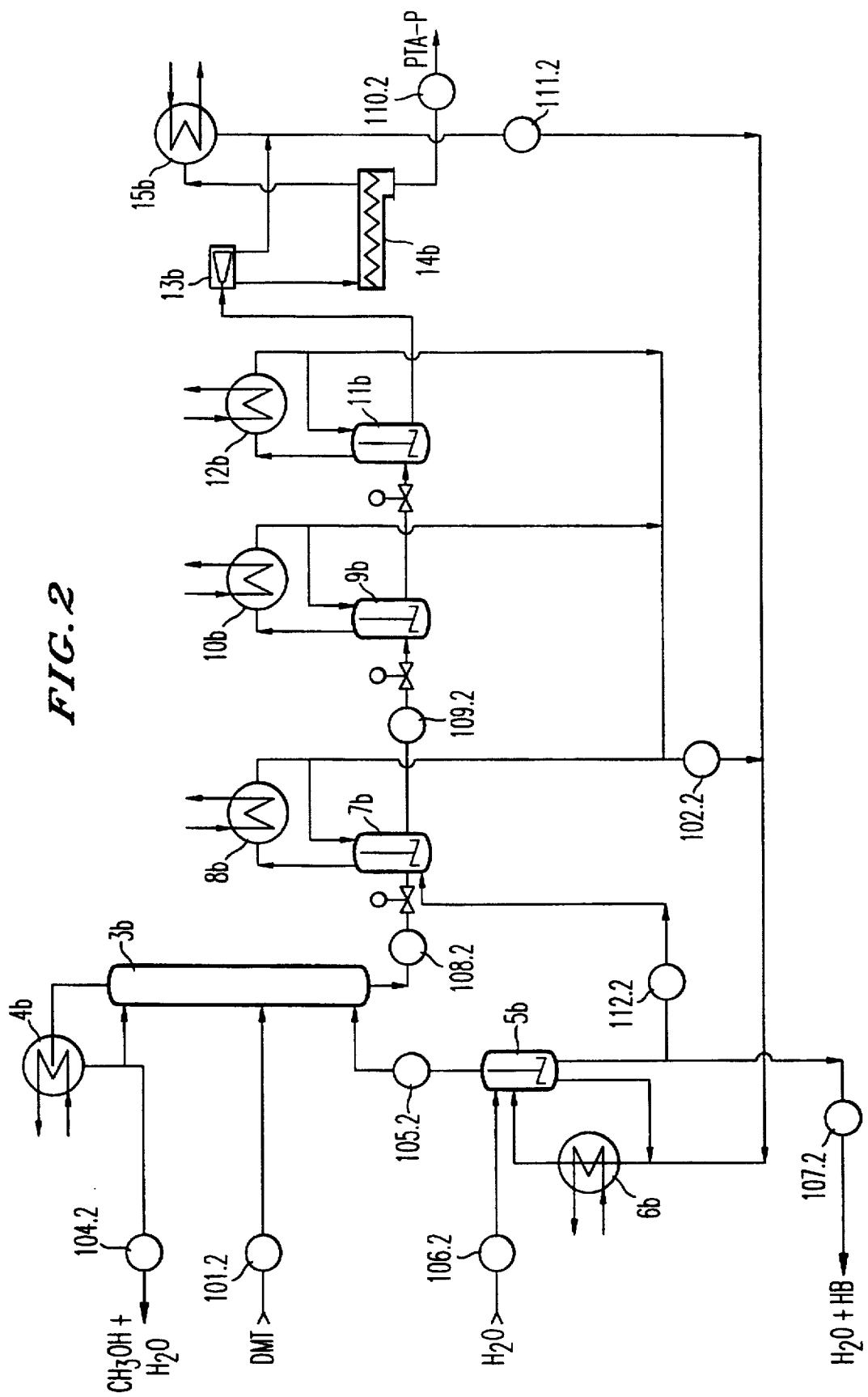
FIG. 2 shows a flow diagram of another preferred embodiment of the process according to the invention 3b: Countercurrent reactor
4b: Condenser, coupled
5b: Evaporator
6b: Heat exchanger
7b, 9b, 11b: Crystallization tank, stirrable
8b, 10b, 12b: Condensers
13b: Decanter
14b: Drier
15b: Condenser

Example 2:

Example 2 is carried out in a plant according to the flow diagram in FIG. 2. FIG. 2 also shows a preferred embodiment of the process according to the invention, a preliminary reactor with a condenser being omitted here. In the present example, the DMT (substance stream 101.2) is fed directly into the reactor 3b. The total added water is added here via substance stream 106.2 into the evaporator 5b with the heat exchanger 6b. A small amount is furthermore removed from the circulation by the substance stream 107.2, this small amount also comprising high-boiling constituents, any foreign particles and a water content which is necessary for problem-free further handling but is comparatively low. The substances contained in the stream 107.2 are thus not recycled to the hydrolysis, which means that the amounts of DMT employed (substance stream 101.2) and water (substance stream 106.2) are increased slightly compared with Example 1. Furthermore, no bottom product from the evaporator 5b is recycled to the process via substance stream 112.2 of the present example. The foreign particles content in the PTA-P is reduced considerably by this procedure, which means that the quality of the TA produced is further improved considerably. The generation of stripping steam is increased somewhat with this procedure. The description of FIG. 2 and the associated procedure otherwise corresponds in principle to that of FIG. 1 and that from Example 1.

The temperatures and the amounts stated for the substance streams—including the components contained therein from Example 2 are to be found in Table 2, the amounts stated in each case relating to a substance stream of 1000 kg of TA per hour.

Legend to the abbreviations used herein and in the Tables:

p-X: para-xylene p-TA: para-toluic acid p-TE: para-toluic acid methyl ester (pT-ester)

HM-BME: hydroxymethylbenzoic acid methyl ester

MM-BME: methoxymethylbenzoic acid methyl ester

DMT: dimethyl terephthalate
MMT: monomethyl terephthalate (terephthalic acid monomethyl ester)
TA: terephthalic acid
MTA: medium-purity terephthalic acid
PTA: high-purity terephthalic acid
PTA-p: very high-, i.e. extremely high-purity terephthalic acid (content of MMT and p-TA together of <50 ppm by weight)
TAS: terephthalaldehyde acid (4-CBA)
TAE: terephthalaldehyde acid methyl ester
DME: dimethyl ether
DMI: dimethyl isophthalic acid
DMO: dimethyl orthophthalic acid
ITA: isophthalic acid
OTA: orthophthalic acid the appended claims, the invention may be practiced otherwise than as specifically described herein.

This application is based on German patent applications 195 02 132.3 and 195 36 814.2 filed Jan. 24, 1995, and Oct. 2, 1995, both incorporated herein by reference.

What is claimed is:

1. A process for the preparation of terephthalic acid from pure dimethyl terephthalate and/or a dimethyl terephthalate intermediate product by hydrolysis in a countercurrent reactor at a conversion of greater than 99% with crystallization to give solid product, wherein that the sum of the stripping steam (S) and reaction water (W) satisfies the relationship $$L \leq S+W \leq 2L,$$

wherein (L) represents the amount of water necessary to keep the terephthalic acid produced largely in solution during the reaction and in the bottom of the reactor, where (S), (L) and (W) are by weight, and wherein the terephthalic

TABLE 1

List of the temperatures and the contents of components of the subtance streams from Example 1, cf. FIG. 1. The amounts are stated in kg and are in each case based on a substance stream of 1000 kg of TA per hour.

| Substance stream | 101,1 | 102,1 | 103,1 | 104,1 | 105,1 | 106,1 | 107.1 | 108,1 | 109,1 | 110,1 | 111,1 | 112,1 |
|---|---|---|---|---|---|---|---|---|---|---|---|---|
| Temperature [°C.] | 160 | — | 100 | 220 | 270 | — | — | 265 | 200 | 100 | 100 | 270 |
| Components [kg] | | | | | | | | | | | | |
| DMT | 1168,63 | — | — | — | — | — | — | — | — | — | — | — |
| TA | — | — | — | — | — | — | — | 999,69 | 1002,94 | 999,94 | 3,0 | 3,29 |
| H$_2$O | — | — | — | 128,52 | 2699,98 | — | — | 2700,0 | 3000,0 | — | 3000,0 | 300 |
| CH$_3$OH | — | — | 345,39 | 385,55 | 0,349 | — | — | 0,3 | 0,3 | — | 0,3 | — |
| MMT | — | — | — | — | — | — | — | 0,3 | 0,3 | 0,025 | 0,275 | — |
| TAE/4-CBA | 0,011 | — | — | — | — | — | — | 0,01 | 0,01 | 0,01 | — | — |
| DMI/IPA | 0,029 | — | — | — | — | — | — | 0,025 | 0,3 | 0,025 | 0,275 | 0,275 |
| Σtotal | 1168,670 | 0 | 345,39 | 514,07 | 2700,33 | 0 | 0 | 3700,625 | 4003,85 | 1000,0 | 3003,85 | 303,52 |

TABLE 2

List of the temperatures and the contents of components of the substance streams from Example 2, cf. FIG. 2. The amounts are stated in kg and are in each case based on a substance stream of 1000 kg of TA per hour.

| Substance stream | 101,1 | 102,2 | 103,2 | 104,2 | 105,2 | 106,2 | 107,2 | 108,2 | 109,2 | 110,2 | 111,2 | 112,2 |
|---|---|---|---|---|---|---|---|---|---|---|---|---|
| Temperature [°C.] | 160 | — | — | 220 | 270 | 100 | 270 | 265 | 200 | 100 | 100 | — |
| Components [kg] | | | | | | | | | | | | |
| DMT | 1172,4 | — | — | — | — | — | — | — | — | — | — | — |
| TA | — | — | — | — | — | — | 3,25 | 1002,94 | 1002,94 | 999,94 | 3,0 | — |
| H$_2$O | — | — | — | 128,96 | 3346,55 | 376,58 | 30,0 | 3000,0 | 3000,0 | — | 3000,0 | — |
| CH$_3$OH | — | — | — | 386,88 | 0,35 | — | — | 0,3 | 0,3 | — | 0,3 | — |
| MMT | — | — | — | — | — | — | — | 0,3 | 0,3 | 0,025 | 0,275 | — |
| TAE/4-CBA | 0,0109 | — | — | — | — | — | — | 0,01 | 0,01 | 0,01 | — | — |
| DMI/IPa | 0,35 | — | — | — | — | — | 0,275 | 0,3 | 0,3 | 0,025 | 0,275 | — |
| Σtotal | 1172,76 | 0 | 0 | 515,78 | 3346,9 | 376,58 | 33,53 | 4003,85 | 4003,85 | 1000,0 | 3003,85 | 0 |

Obviously, numerous modifications and variations of the present invention are possible in light of the above teachings. It is therefore to be understood that within the scope of acid produced is crystallized in a crystallization which is free from washing stages.

2. The process according to claim 1, wherein the countercurrent reactor is equipped with more than 20 and up to 200 exchange plates.

3. The process according to claim 2, wherein the countercurrent reactor is equipped with more than 40 and up to 200 exchange plates.

4. The process according to claim 1, wherein the content of monomethyl terephthalate in aqueous solution in the bottom of the reactor is depleted to from 10 to 5000 ppm by weight by stripping by means of steam.

5. The process according to claim 4, wherein the content of monomethyl terephthalate in the aqueous solution in the bottom of the reactor is depleted to from 10 to less than 900 ppm by weight by stripping by means of steam.

6. The process according to claim 5, wherein the content of monomethyl terephthalate in the aqueous solution in the bottom of the reactor is depleted to less than 50 ppm by weight by stripping by means of steam.

7. The process according to claim 1, wherein the reaction water is employed for mixing with the dimethyl terephthalate and then the mixture is passed to the reactor, or the reaction water is passed directly to the reactor, or part of the reaction water is employed for mixing with the dimethyl terephthalate and then the mixture is passed to the reactor, and the other part of the reaction water is passed directly to the reactor, the ratio of the reaction water (W) to stripping steam (S), (W):(S), based on weight, being in the range from 1:1 to 4:1.

8. The process according to claim 7, wherein the reaction water is employed for mixing with the dimethyl terephthalate and then the mixture is passed to the reactor, or the reaction water is passed directly to the reactor, or part of the reaction water is employed for mixing with the dimethyl terephthalate and then the mixture is passed to the reactor, and the other part of the reaction water is passed directly to the reactor, the ratio of reaction water (W) to stripping steam (S), based on weight, being in the range from 1:1 to 1.5:1.

9. The process according to claim 8, wherein the reaction water is employed for mixing with the dimethyl terephthalate and then the mixture is passed to the reactor, or the reaction water is passed directly to the reactor, or part of the reaction water is employed for mixing with the dimethyl terephthalate and then the mixture is passed to the reactor, and the other part of the reaction water is passed directly to the reactor, the ratio of reaction water (W) to stripping steam (S), based on weight, being 1:1.

10. The process according to claim 1, wherein the weight ratio of stripping steam (S) employed to dimethyl terephthalate is 1:1 to 6:1.

11. The process according to claim 10, wherein that the weight ratio of stripping steam (S) employed to dimethyl terephthalate is 2:1 to 4:1.

12. The process according to claim 1, wherein the countercurrent reactor is charged with a reflux which is capable of keeping the terephthalic acid in the bottom of the reactor in solution.

13. The process according to claim 1, wherein a preliminary reactor in the form of a stirred tank or a cascade of stirred tanks or a flow tube is employed.

14. The process according to claim 1, wherein methanol is removed from circulation in or after any preliminary reactor.

15. The process according to claim 1, wherein high-quality steam which is suitable for stripping steam with a heat pump, is generated during partial or total condensation of vapors leaving the reactor, all or some of the liquid phase produced being recycled to the reactor.

16. The process according to claim 1, wherein that the water obtained in the crystallization is separated off, recycled to the process and employed in any desired ratios together for generation of stripping steam and/or reaction water.

17. The process according to claim 1, wherein that traces of impurities are removed from circulation via generation of stripping steam.

18. The process according to claim 1, wherein that water is removed from circulation at various temperature levels in the one- or multi-stage crystallization and recycled to the process.

19. The process according to claim 1, wherein that the methanol obtained is employed again as the raw material in a dimethyl terephthalate plant.

20. The process according to claim 1, wherein that solids are partly obtained during the hydrolysis.

* * * * *